United States Patent
Sugimoto et al.

(10) Patent No.: US 9,061,081 B2
(45) Date of Patent: Jun. 23, 2015

(54) ATMOSPHERE-CLEANING DEVICE EQUIPPED ON VEHICLE AND METHOD FOR MANUFACTURING SAME

(75) Inventors: Kazuhiro Sugimoto, Susono (JP); Yoshihisa Shinoda, Susono (JP); Kazuhiro Fukumoto, Nagoya (JP); Kenichirou Suzuki, Owariasahi (JP)

(73) Assignees: TOYOTA JIDOSHA KABUSHIKI KAISHA, Toyota-shi (JP); KABUSHIKI KAISHA TOYOTA CHUO KENKYUSHO, Aichi-gun (JP)

( * ) Notice: Subject to any disclaimer, the term of this patent is extended or adjusted under 35 U.S.C. 154(b) by 0 days.

(21) Appl. No.: 14/123,400

(22) PCT Filed: Dec. 7, 2011

(86) PCT No.: PCT/JP2011/078266
§ 371 (c)(1),
(2), (4) Date: Dec. 2, 2013

(87) PCT Pub. No.: WO2012/164775
PCT Pub. Date: Dec. 6, 2012

(65) Prior Publication Data
US 2014/0105791 A1 Apr. 17, 2014

(30) Foreign Application Priority Data
Jun. 3, 2011 (JP) .................. 2011-125265

(51) Int. Cl.
*B01J 20/34* (2006.01)
*B01J 31/00* (2006.01)
(Continued)

(52) U.S. Cl.
CPC .............. *A61L 9/00* (2013.01); *B01D 53/8675* (2013.01); *F01P 11/12* (2013.01);
(Continued)

(58) Field of Classification Search
CPC .......... A61L 9/014; A61L 9/205; B01J 20/00; B01J 21/00; C23C 18/31
USPC ......... 510/376; 502/34, 102, 400, 515; 422/5, 422/122, 177, 211, 312, 900; 55/108; 252/88.2; 427/332, 301
See application file for complete search history.

(56) References Cited

U.S. PATENT DOCUMENTS 6,340,066 B1 * 1/2002 Dettling et al. .............. 180/54.1
6,699,529 B2 3/2004 Garner et al.

FOREIGN PATENT DOCUMENTS

| JP | 2002-514966 | 5/2002 |
| JP | 2006-176698 | 7/2006 |

(Continued)

OTHER PUBLICATIONS

International Search Report issued Feb. 7, 2012, in PCT/JP11/078266 filed Dec. 7, 2011.

*Primary Examiner* — Monzer R Chorbaji
(74) *Attorney, Agent, or Firm* — Oblon, McClelland, Maier & Neustadt, L.L.P.

(57) ABSTRACT

An atmosphere-cleaning device equipped on vehicle and provides a DOR (Direct Ozone Reduction) system including an on-vehicle component on which a new ozone purifier is supported and a method for manufacturing same. A radiator has a core part including an ozone purifier with a particle of an activated carbon as its core and an ozone purification catalyst layer as its shell formed by powder plating process. Ozone can diffuse into the layer and the carbon in this order. Ozonolysis reaction with the sub-catalyst can be initiated in advance to ozonolysis reaction with the carbon thereby gas contact probability with the carbon can be relatively reduced and oxidation reaction of the carbon caused by active oxygen can be suppressed.

6 Claims, 10 Drawing Sheets

(51) Int. Cl.
*C09K 3/22* (2006.01)
*A61L 9/00* (2006.01)
*B01D 53/86* (2006.01)
*B01J 21/18* (2006.01)
*B01J 23/40* (2006.01)
*B01J 23/46* (2006.01)
*B01J 23/74* (2006.01)
*B01J 35/00* (2006.01)
*B01J 23/42* (2006.01)
*F01P 11/12* (2006.01)
*B01J 23/14* (2006.01)
*B01J 23/72* (2006.01)
*B01J 23/44* (2006.01)
*B01J 23/50* (2006.01)
*B01J 23/52* (2006.01)
*B01J 23/745* (2006.01)
*B01J 23/75* (2006.01)
*B01J 23/755* (2006.01)

(52) U.S. Cl.
CPC ............ *B01D 2255/1021* (2013.01); *B01D 2255/1023* (2013.01); *B01D 2255/1025* (2013.01); *B01D 2255/1026* (2013.01); *B01D 2255/1028* (2013.01); *B01D 2255/104* (2013.01); *B01D 2255/106* (2013.01); *B01D 2255/20738* (2013.01); *B01D 2255/20746* (2013.01); *B01D 2255/20753* (2013.01); *B01D 2255/20761* (2013.01); *B01D 2255/2094* (2013.01); *B01D 2255/702* (2013.01); *B01D 2258/06* (2013.01); *B01D 2259/4566* (2013.01); *B01J 21/18* (2013.01); *B01J 23/14* (2013.01); *B01J 23/40* (2013.01); *B01J 23/46* (2013.01); *B01J 23/72* (2013.01); *B01J 23/74* (2013.01); *B01J 35/008* (2013.01); *B01J 23/42* (2013.01); *B01J 23/44* (2013.01); *B01J 23/462* (2013.01); *B01J 23/464* (2013.01); *B01J 23/466* (2013.01); *B01J 23/468* (2013.01); *B01J 23/50* (2013.01); *B01J 23/52* (2013.01); *B01J 23/745* (2013.01); *B01J 23/75* (2013.01); *B01J 23/755* (2013.01)

(56) References Cited

FOREIGN PATENT DOCUMENTS

| | | |
|---|---|---|
| JP | 2009-208018 | 9/2009 |
| JP | 2009-254961 | 11/2009 |
| JP | 2012-236144 | 12/2012 |
| WO | WO 96/22146 | 7/1996 |

* cited by examiner (A)

(B)

ATMOSPHERE-CLEANING DEVICE EQUIPPED ON VEHICLE AND METHOD FOR MANUFACTURING SAME

TECHNICAL FIELD

The present invention relates to an atmosphere-cleaning device equipped on vehicle and a method for manufacturing same. More practically, the present invention relates to the atmosphere-cleaning device equipped on vehicle capable of purifying ozone in atmosphere and the method for manufacturing same.

BACKGROUND ART

Ozone, which causes photochemical smog, is produced by a photochemical reaction of HC and NOx contained in exhaust gases from vehicles and factories. Therefore, reducing the amount of emissions of HC and NOx from vehicles is an efficient way to suppress the production of ozone and the occurrence of photochemical smog. Also, purifying ozone in the atmosphere directly can be one of the ways to prevent the occurrence of photochemical smog. By purifying ozone as a product as well as reducing the amount of emissions of HC and NOx as reactants, the occurrence of photochemical smog can be prevented more effectively. In this respect, an vehicle including an atmosphere-cleaning device equipped on vehicle capable of directly purifying ozone in the atmosphere has been put into practical use in some places including California in the United States of America. This atmosphere-cleaning device equipped on vehicle, specifically, is called a DOR (Direct Ozone Reduction) system.

For example, Patent Literature 1 discloses a DOR system in which a metal oxide such as manganese dioxide is supported by an on-vehicle component. An on-vehicle component such as a radiator is disposed at a spot in contact with atmosphere during travel of the vehicle, and manganese dioxide has a function of converting ozone contained in the atmosphere into other substances such as oxygen, and purifying ozone. Therefore, according to the DOR system disclosed in Patent Literature 1, ozone in the atmosphere can be directly purified during travel of the vehicle.

CITATION LIST

Patent Literature

Patent Literature 1: National Publication of International Patent Application No. 2002-514966
Patent Literature 2: Japanese Patent Laid-Open Publication No. 2006-176698

SUMMARY OF INVENTION

As an ozone purifier, however, metal oxide including manganese dioxide is very expensive. Therefore, to establish future widespread use of the DOR system, it is necessary to develop new ozone purifiers which can be used as an alternative to the metal oxide. In addition, an on-vehicle component on which an ozone purifier is supported is generally manufactured for anything purposes but purifying ozone. Thus, in order to familiarize the use of the DOR system, it is necessary to develop an inexpensive manufacturing method for supporting the ozone purifier without taking apart the on-vehicle component.

The present invention has been made in view of the above-described circumstances. It is an object to provide a DOR system including an on-vehicle component on which a new ozone purifier is supported and a method for manufacturing same.

Means for Solving the Problem

To achieve the above mentioned purpose, a first aspect of the present invention is an atmosphere-cleaning device equipped on vehicle, comprising:
an on-vehicle component arranged on a portion where an air flow passage is formed while a vehicle is moving; and
an ozone purifier provided on the surface of the on-vehicle component, said ozone purifier including an ozone purification catalyst which contains two or more metals each of which has a different standard electrode potential.

A second aspect of the present invention is the atmosphere-cleaning device equipped on vehicle according to the first aspect, wherein
said ozone purifier further includes an ozone purification material which has a function of purifying ozone.

A third aspect of the present invention is the atmosphere-cleaning device equipped on vehicle according to the second aspect, wherein
said ozone purification material is a porous body capable of supporting said ozone purification catalyst.

A forth aspect of the present invention is the atmosphere-cleaning device equipped on vehicle according to the third aspect, wherein
said ozone purification material is an activated carbon, and
particle surface of said activated carbon is covered with said ozone purification catalyst.

A fifth aspect of the present invention is the atmosphere-cleaning device equipped on vehicle according to any one of the first to the forth aspects, wherein
said on-vehicle component is a radiator, and
said ozone purifier is a single layer formed on the surface of said radiator.

A sixth aspect of the present invention is the atmosphere-cleaning device equipped on vehicle according to any one of the first to the fifth aspects, wherein
said ozone purification catalyst includes a first catalyst element whose main element is at least one metal selected from the group of Co, Ni, Cu, Fe, Sn, Rh, Ir, Pd, Pt, Ag, Au, Ru and Os, and a second catalyst element which is supported on said first catalyst element and whose main element is a metal with higher standard electrode potential than the metal used as the main element of said first catalyst element.

To achieve the above mentioned purpose, a seventh aspect of the present invention is a method for manufacturing an atmosphere-cleaning device equipped on vehicle according to any one of the first to the sixth aspects, comprising:
a process of preparing an ozone purifier, by electroless plating process, which includes an ozone purification catalyst containing two or more metals each of which has a different standard electrode potential; and
a process of preparing slurry said ozone purifier and applying the slurry, by spraying, on the surface of said on-vehicle component.

Advantageous Effects of Invention

According to the first aspect of the present invention, since the ozone purifier includes the ozone purification catalyst containing two or more metals each of which has a different standard electrode potential, ozone in atmosphere can be purified with potential differences occurred between these metals.

According to the second aspect of the present invention, ozone in the atmosphere can be purified by the ozone purification material in addition to the ozone purification catalyst.

According to the third aspect of the present invention, since the ozone purification catalyst can be supported in large amount by the porous body, an efficiency of ozone purification by the ozone purifier can be enhanced.

According to the fourth aspect of the present invention, since the particle surface of the activated carbon is covered with the ozone purification catalyst, ozone in the atmosphere can contact to the ozone purification catalyst and the activated carbon particle in this order. Therefore, an ozonolysis reaction with the ozone purification catalyst can be initiated unfailingly in advance to ozonolysis reaction with the activated carbon. In addition, the ozone purification catalyst has a function of purifying active oxygen, which enables to purify the active oxygen generated by the ozonolysis reaction with the activated carbon promptly by the ozone purification catalyst located near the generated active oxygen. Therefore, a deterioration of the ozone purification function of the ozone purifier can be suppressed favorably.

According to the fifth aspect of the present invention, since the ozone purifier is a single layer formed on the surface of the radiator, it makes possible to form thinner layer than a case, for example, where the ozone purifier is formed as multiple layers of an activated carbon layer and an ozone purification catalyst layer. Therefore, a decrease in the cooling function of the radiator caused by the formation of the ozone purifier can be minimized.

According to the sixth aspect of the present invention, since the main element of the second element is the metal with higher standard electrode potential than the metal used as the main element of the first catalyst element, the ozonolysis reaction can be developed with the difference of potential occurred between the first element and the second element.

According to the seventh aspect of the present invention, the ozone purifier can be supported to the on-vehicle component inexpensively without taking apart the on-vehicle component in manufacturing the atmosphere-cleaning device equipped on vehicle according to any one of the first to the sixth aspects.

DESCRIPTION OF EMBODIMENTS

[Configuration of an Atmosphere-Cleaning Device Equipped on Vehicle]

Figure 1:
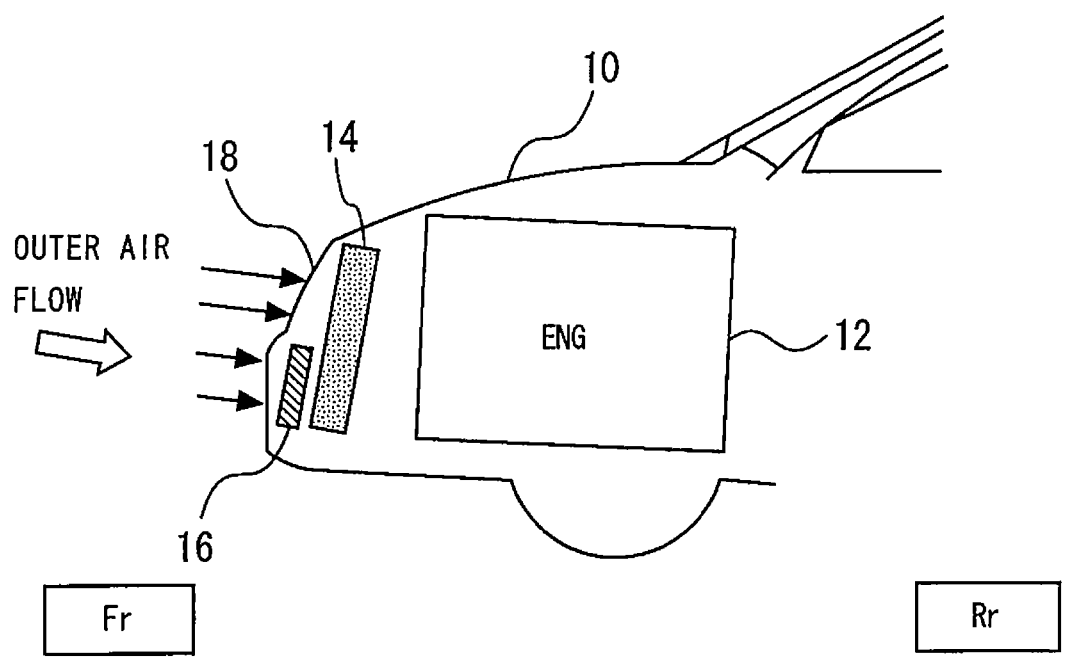
FIG. 1 is a schematic view showing a structure of a vehicle on which an atmosphere-cleaning device according to an embodiment of the present invention is applied.

An embodiment of the present invention will be explained below with reference to FIGS. 1 to 8. FIG. 1 is a schematic view showing a structure of a vehicle on which an atmosphere-cleaning device according to an embodiment of the present invention is applied. The vehicle 10 includes a internal combustion 12 serving as a power unit. The exhaust gas discharged from the internal combustion 12 contains HC and NOx. Ozone is produced by photochemical reaction between HC and NOx as reactants. Therefore, the atmosphere-cleaning device equipped on vehicle is applied on the vehicle 10 comprising the internal combustion 12, the ozone is purified while the vehicle 10 is moving, and thus, the damage to the environment caused due to the vehicle 10 can be reduced.

A radiator 14 for cooling coolant water circulating through the internal combustion 12 is arranged on the front side of the internal combustion 12. A capacitor 16 of an air conditioner is mounted on the front side of the radiator 14. As shown by arrows in FIG. 1, outer air is taken in through a bumper grill 18 arranged on a front surface of the vehicle 10 during travel of the vehicle 10 and the taken air is delivered through the capacitor 16 and the radiator 14 in this order to be discharged to the rear side.

Figure 2:
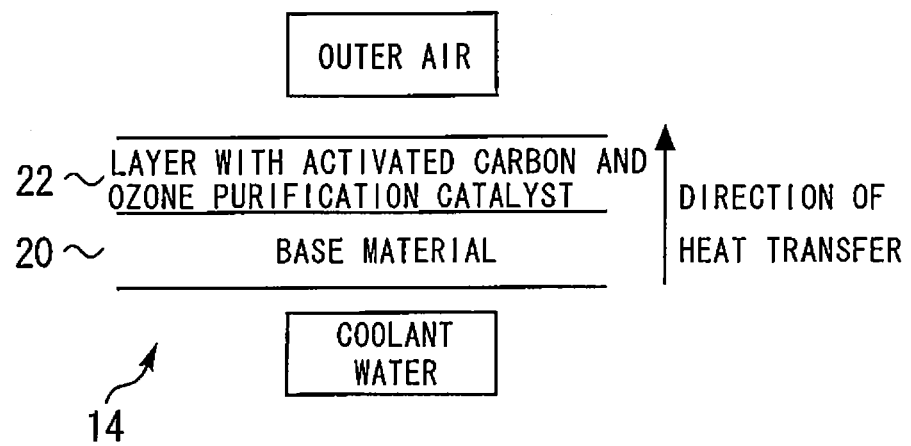
FIG. 2 is a typical cross-section showing a core part of the radiator 14 of FIG. 1.

Next, a detailed configuration of the radiator 14 will be described with reference to FIG. 2. FIG. 2 is a typical cross-section showing a core part of the radiator 14 of FIG. 1. As shown in FIG. 2, a core part of the radiator 14 is configured by coating an ozone purifier layer 22 on a base material 20. The base material 20 includes aluminum alloy or the like which have high thermal conductivity and transfers heat of the coolant from the side of the base material 20 to the side of the ozone purifier layer 22. The ozone purifier layer 22 includes a catalyst having a function of purifying ozone (hereinafter referred to as "ozone purification catalyst"), an ozone purifier consisted of activated carbon and a binder which adheres the catalyst and the ozone purifier to each other.

[Ozone Purifier]

Since the activated carbon, which is included in the ozone purifier layer 22, has a function of purifying ozone as well as metal oxide such as manganese dioxide and is available at moderate price, it has been expected to be used as an alternative to the metal oxide. The activated carbon can purify ozone not only in temperature region where coolant flows through a radiator for an engine (typically 80° C. to 100° C.) or a radiator for a hybrid engine (typically 50° C. to 70° C.) but also in ambient temperature region (typically 25° C.). And thus the activated carbon has an advantage over the metal oxide which requires a higher temperature than 80° C. for purifying ozone.

Figure 3:
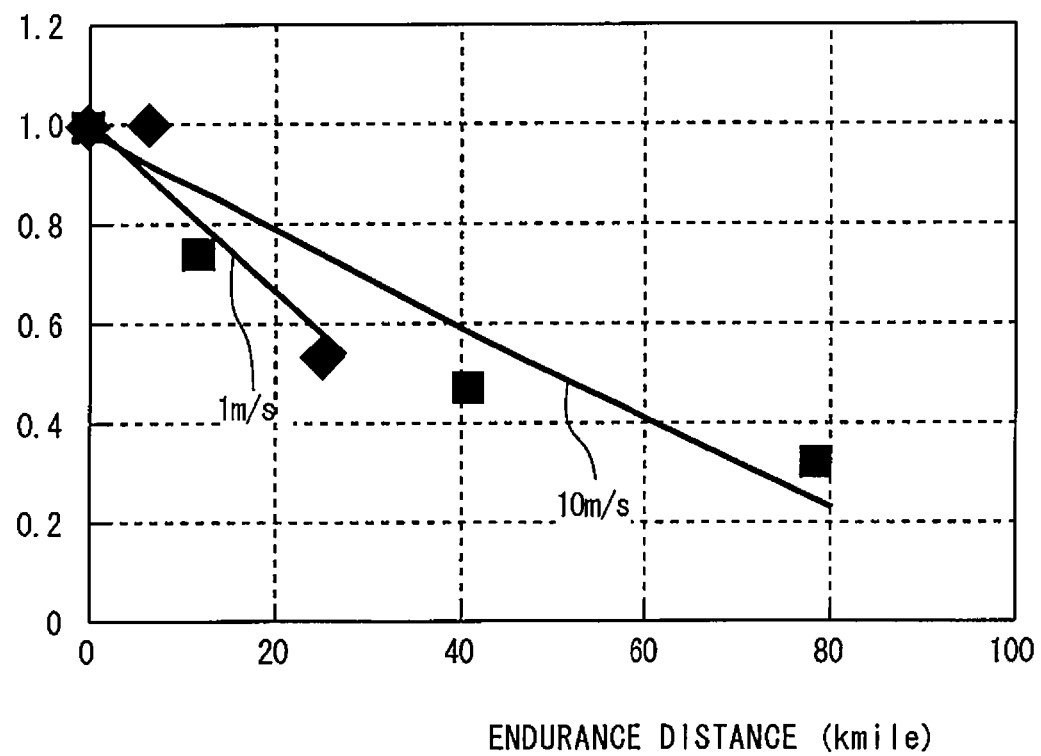
FIG. 3 is a data showing results of an ozone purification endurance test.

However, there is a problem that when the activated carbon is used as an ozone purifier, its ozone purifying function is easily deteriorated. FIG. 3 shows data of results of an ozone purification endurance test. In FIG. 3, the horizontal axis represents an endurance distance (in kilomiles) and the vertical axis represents a relative value based on an ozone purification rate at an initial state (when the endurance distance is 0 kilomiles). The data shown in FIG. 3 is obtained by preparing two activated carbons of equivalent sizes and specific surface areas, and then measuring the rear side ozone level of the two activated carbons by blowing a gas which contains ozone with a predetermined level through these activated carbons from the front side toward the rear side at different velocities (wind velocities of 1 m/s and 10 m/s).

As shown in FIG. 3, the ozone purification rate of the activated carbon is reduced as the endurance distance becomes longer. Also, as shown in FIG. 3, the degree of reduction of the ozone purification rate of the activated carbon is changed depending on the wind velocity of the passing gas containing ozone. More specifically, in the case where the gas containing the ozone passes at the wind velocity of 1 m/s, the ozone purification rate goes down by half from the ozone purification rate at the initial state when the endurance distance is approximately 30 kilomiles. In the case where the gas containing the ozone passes at the wind velocity of 10 m/s, the ozone purification rate goes down by half from the purification rate at the initial state when the endurance distance is approximately 50 kilomiles. In other words, the degree of reduction of the ozone purification rate is smaller when the gas passes at high speed (wind velocity of 10 m/s) as compared to when the gas passes at low speed (wind velocity of 1 m/s).

Figure 4:
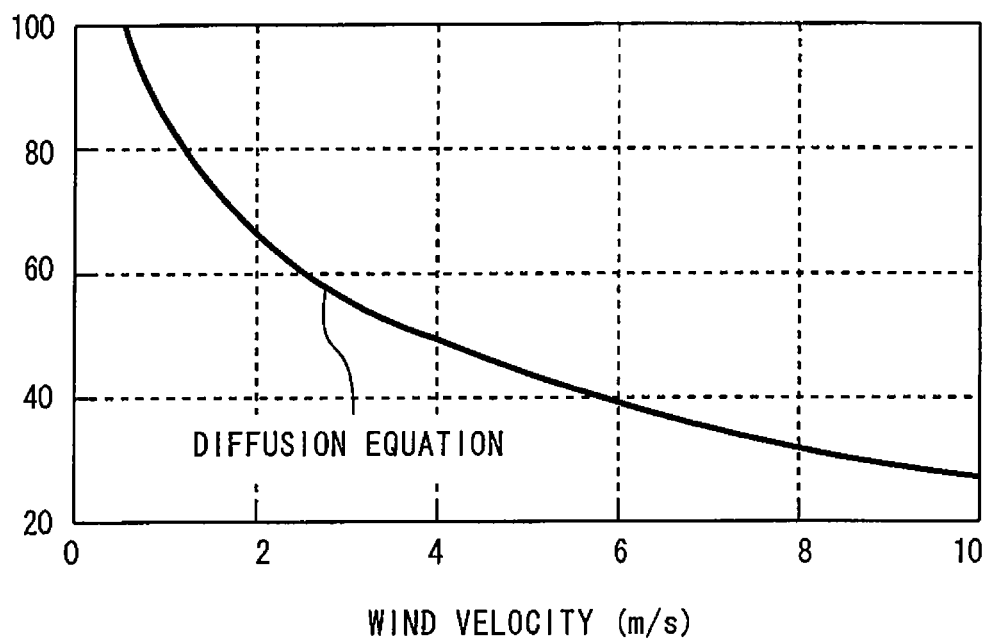
FIG. 4 is a graph showing a relationship between wind velocity of gas passing through a radiator and probability that the gas is contacted with the radiator.
Figure 5:
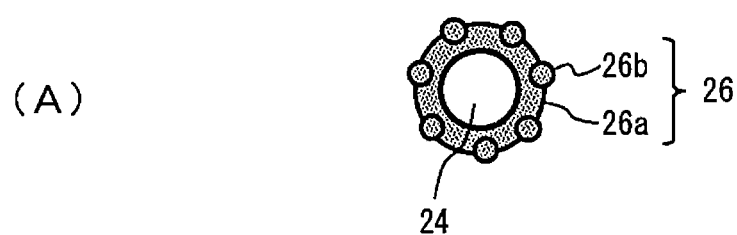
FIG. 5 is a schematic view showing a particle of the ozone purifier contained in an ozone purifier layer 22 of FIG. 2 (FIG. 5(A)) and an enlarged cross-section near the surface of the particle of FIG. 5(A) (FIG. 5(B)).
Figure 5:
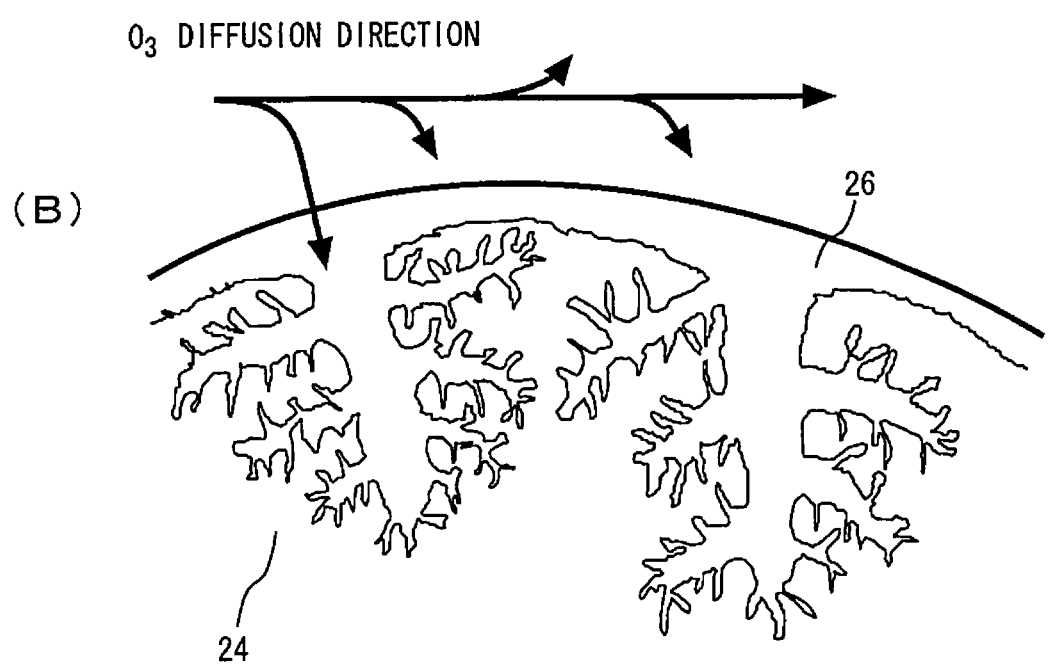

FIG. 4 is a graph showing a relationship between the wind velocity of a gas passing through a radiator and the probability that the gas is contacted with the radiator (hereinafter referred to as "gas contact probability"). This graph is provided by applying the Gormley-Kennedy diffusion equation to a model of an aluminum honeycomb radiator. As shown in FIG. 4, the probability that the gas is contacted with the radiator is approximately 100% when the wind velocity is approximately 1 m/s. Also, the probability that the gas is contacted with the radiator is decreased to approximately 10% when the wind velocity is approximately 10 m/s. In other words, the probability that the gas is contacted with the radiator is high when the wind velocity is slow, and is gradually lowered as the wind velocity is faster.

From the graphs shown in FIGS. 3 and 4, it is found that the ozone purification rate of the activated carbon and gas contact probability correlate with each other. It is found from the graph shown in FIG. 4 that gas contact probability is higher as the wind velocity is slower and gas contact probability is lower as the wind velocity is faster. Also, it is found from the graph shown in FIG. 3 that the degree of reduction of the ozone purification rate is larger as the wind velocity is slower and the degree of reduction of the ozone purification rate is smaller as the wind velocity is faster. Accordingly, from the graphs in FIGS. 3 and 4, it is obvious that the degree of reduction of the ozone purification rate of the activated carbon is greater as gas contact probability is higher and the degree of reduction of the ozone purification rate of the activated carbon is lesser as gas contact probability is lower.

The inventors estimate that the reason why the ozone purification rate of the activated carbon and gas contact probability correlate with each other as described above is because of an ozonolysis mechanism of the activated carbon and aging of the inner structure of the activated carbon. First, the ozonolysis mechanism of the activated carbon will be explained below. The activated carbon has countless fine pores extend from its surface toward its inner side. When ozone molecules enter into such fine pores, electrons are provided from the activated carbon and activation energy of an ozonolysis reaction is reduced. Consequently, ozone is converted into oxygen and active oxygen. The ozonolysis reaction of the activated carbon is represented specifically by the following expressions (1) and (2).

$$O_3 \rightarrow O_3^- \quad (1)$$

$$O_3^- \rightarrow O_2 + O^- \quad (2)$$

Next, the aging of the inner structure of the activated carbon will be explained below. The active oxygen ($O^-$) produced by the ozonolysis reaction of the activated carbon serves as an oxidant of the activated carbon. Since this active oxygen has strong oxidizing power, the activated carbon is oxidized when the active oxygen enter into the fine pores of the activated carbon. Thus, the ozone purifying function of the activated carbon may disappear. The oxidation reaction of the activated carbon caused by the active oxygen is represented specifically by the following expressions (3) and (4).

$$C + O \rightarrow CO \quad (3)$$

$$C + 2O \rightarrow CO_2 \quad (4)$$

In the embodiment of the present invention, therefore, the ozone purification catalyst is used in the ozone purifier layer 22. The ozone purification catalyst has a function of purifying ozone as well as the activated carbon. The ozonolysis reaction of the ozone purification catalyst is represented specifically by the following expressions (5) and (6).

$$O_3 \rightarrow O_3^- \quad (5)$$

$$O_3^- \rightarrow O_2 + O^- \quad (6)$$

The reaction represented by the expressions (5) and (6) is the same as the reaction represented by the expressions (1) and (2). Thus, by using the ozone purification catalyst with the activated carbon, gas contact probability with the activated carbon can be relatively reduced and also the ozone purification represented by the expressions (5) and (6) can be proceeded.

In addition, the ozone purification catalyst also has a function of converting the active oxygen produced by the ozonolysis reaction of the activated carbon into oxygen. The reaction of the active oxygen caused specifically by the ozone purification catalyst is represented by the following expression (7).

$$O^- + O_3^- \rightarrow 2O_2 \quad (7)$$

The reactants of the reaction represented by the expression (7), that is $O_3^-$ and $O^-$, are produced by the reaction represented by the expressions (1) and (2) as well as the reaction represented by the expressions (5) and (6). Therefore, by using the ozone purification catalyst with the activated carbon, the oxidation reaction (the reaction represented by the expressions (3) and (4)) of the activated carbon caused by the active oxygen can be suppressed.

FIG. 5(A) is a schematic view showing a particle of the ozone purifier contained in an ozone purifier layer 22 of FIG. 2. The particle shown in FIG. 5(A) makes a core-shell structure with a particle of an activated carbon 24 (average particle size is 0.02 to 100 μm, preferably 0.1 to 10 μm)) as the core and an ozone purification catalyst layer 26 (layer thickness is 0.1 to 50 μm) as the shell formed by powder plating process (electroless plating process). The ozone purification catalyst layer 26 includes a first catalyst element 26a which is arranged so as to cover around the activated carbon particle 24 and a second catalyst element 26b which is supported on the surface of the first catalyst element 26a.

The main element of the first catalyst element 26a or that of the second catalyst element 26b is at least one metal selected from the group of Co, Ni, Cu, Fe, Sn, Rh, Ir, Pd, Pt, Ag, Au, Ru and Os. The term "main element" means that the first catalyst element 26a or the second catalyst element 26b may include other elements except the above mentioned metals. The first catalyst element 26a and the second catalyst element 26b are composed of a combination of two metals between which a potential difference occurs. The reason for this is to reduce ozone by the potential difference. In order to progress the

ozone reduction effectively, the standard electrode potential of the second catalyst element 26b is preferably higher, more preferably 0.3 V or higher than that of the first catalyst element 26a.

FIG. 5(B) is an enlarged cross-section near the surface of the particle of FIG. 5(A). As shown by arrows in FIG. 5(B), when the ozone purification catalyst layer 26 is formed on the surface of the activated carbon 24, ozone in the atmosphere can diffuse into the ozone purification catalyst layer 26 and the activated carbon 24 in this order. Therefore, an ozonolysis reaction with the ozone purification catalyst can be initiated in advance to the ozonolysis reaction with the activated carbon thereby gas contact probability with the activated carbon can be relatively reduced even more. In addition, it enables to purify the active oxygen generated by the ozonolysis reaction with the activated carbon promptly by the ozone purification catalyst located near the generated active oxygen. Therefore, a deterioration of the ozone purification function of the activated carbon can be suppressed favorably.

Figure 6:
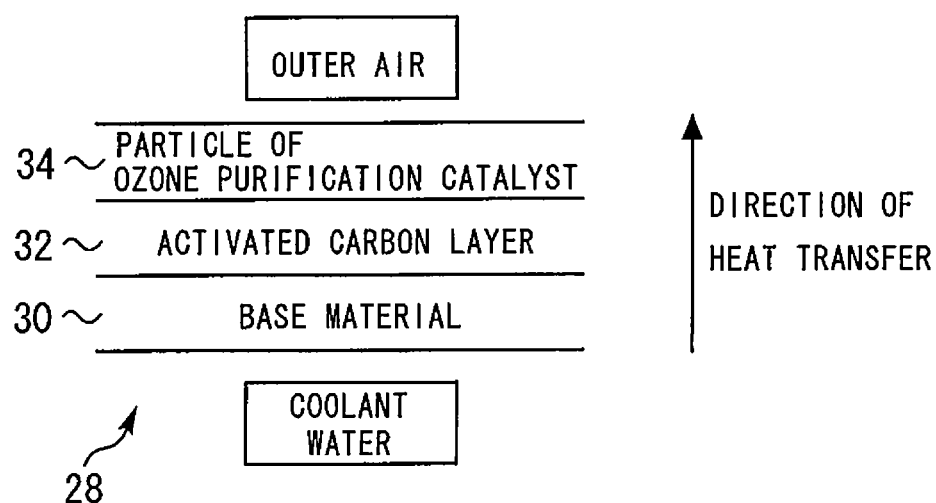
FIG. 6 is a cross section showing a core part for comparing with the core part of FIG. 2.
Figure 7:
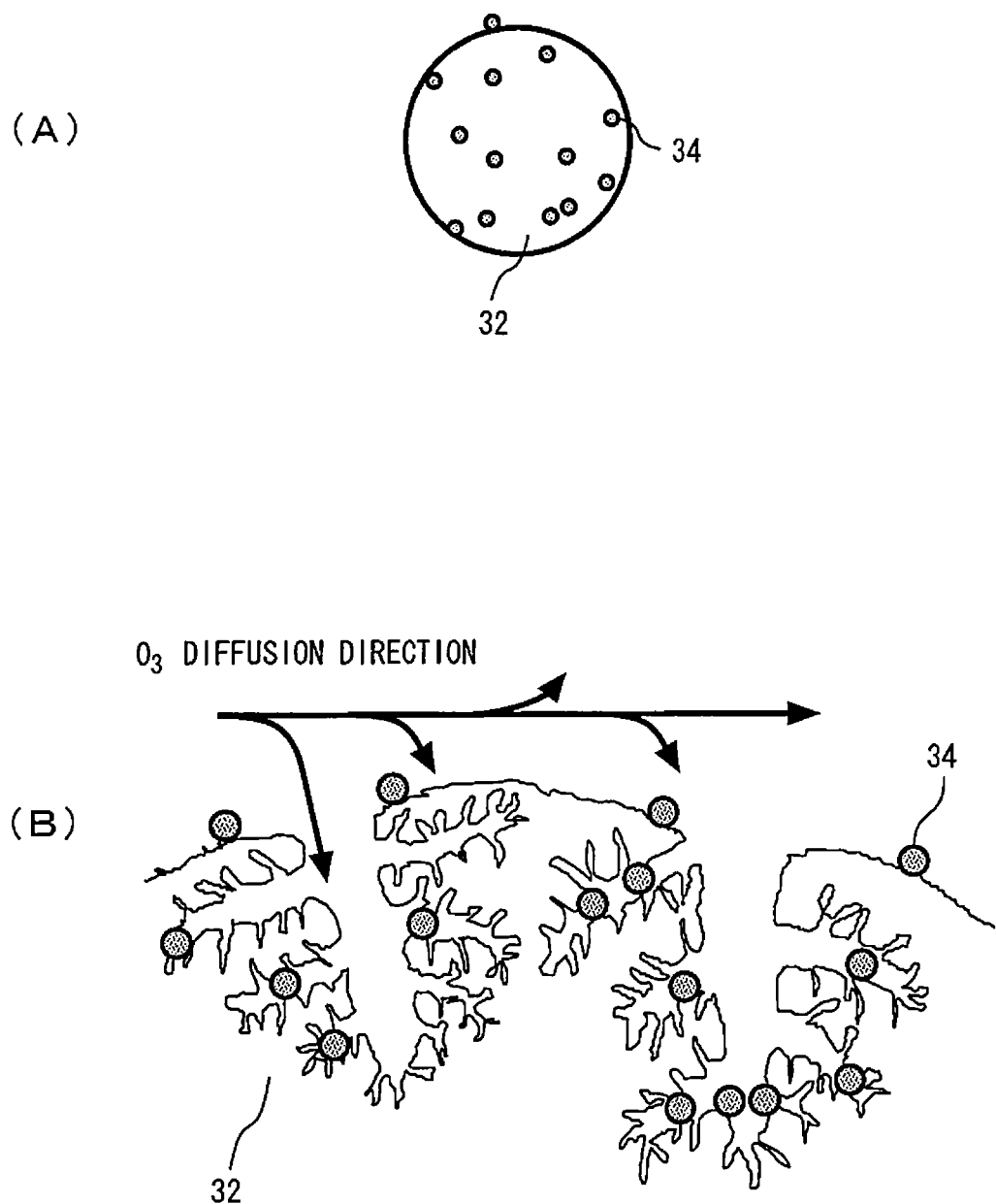
FIG. 7 is a partial cross-section of the core part of the radiator 28 of FIG. 6 (FIG. 7(A)) and a typical cross-section near the surface of the activated carbon layer 32 of FIG. 7(A) (FIG. 7(B)).

Next, the advantageous effects due to the configuration of the core part of the radiator 14 will be explained with reference to FIGS. 6 to 8. FIG. 6 is a cross section showing a core part for comparing with the core part of FIG. 2. As shown in FIG. 6, a core part of a radiator 28 is configured by coating an activated carbon layer 32 on a base material 30 while supporting particles of an ozone purification catalyst 34 in dispersed form on the activated carbon layer 32. In other words, the core part of FIG. 6 has a two-coating layered structure with the activated carbon layer 32 and the layer of the ozone purification catalyst particles 34 that are formed on the base material 30. Therefore, the whole thickness of the radiator 28 increases just for the ozone purification catalyst particles 34. Then, it takes more time to transfer heat of the coolant and thus cooling efficiency of the internal combustion is highly likely to be reduced.

FIG. 7(A) is a partial cross-section of the core part of the radiator 28 of FIG. 6. As shown in FIG. 7(A), the core part of FIG. 6 is configured by supporting particles of an ozone purification catalyst 34 in dispersed form on the activated carbon layer 32. FIG. 7(B) is a typical cross-section near the surface of the activated carbon layer 32 of FIG. 7(A). As shown in FIG. 7(B), the ozone purification catalyst particles 34 are supported on the surface of the activated carbon layer 32 and its fine pores. Therefore, the oxidation reaction of the activated carbon caused by the active oxygen (i.e. the reaction represented by the expressions (3) and (4)) can be suppressed by the function of ozone purification catalyst included in the particles 34. However, to fulfill the function, it is necessary to support the ozone purification catalyst particles 34 on the activated carbon layer 32 where ozone and active oxygen can react promptly therewith. If dispersion state of the ozone purification catalyst particles 34 is inadequate, the activated carbon layer 32 is oxidized to be deteriorated locally and the ozone purification with the activated carbon layer 32 becomes less uniform.

Figure 8:
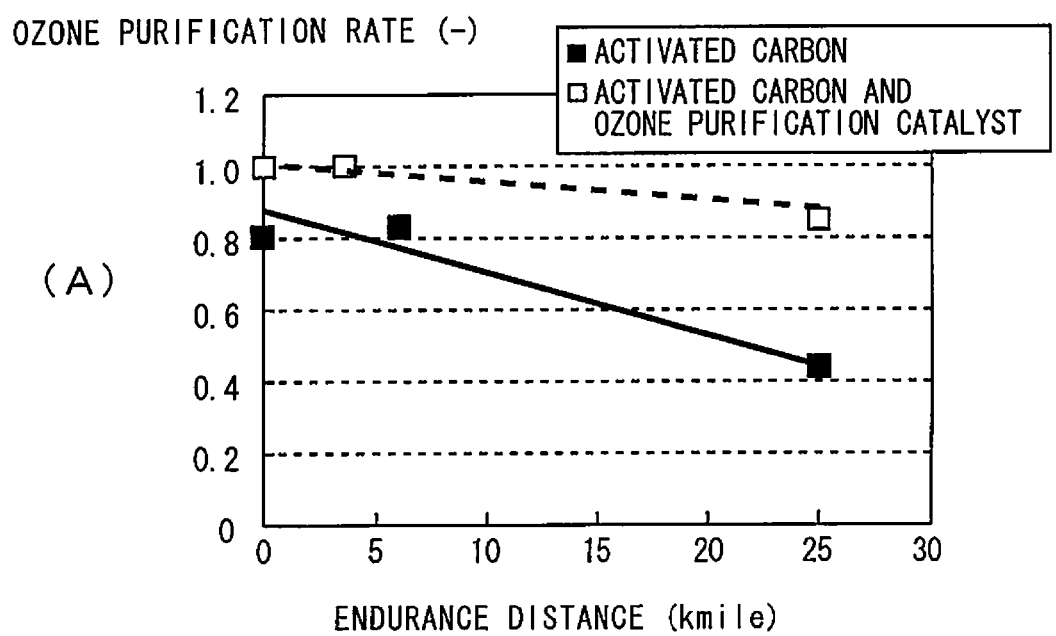
FIG. 8 is a data showing results of an ozone purification endurance test.
Figure 8:
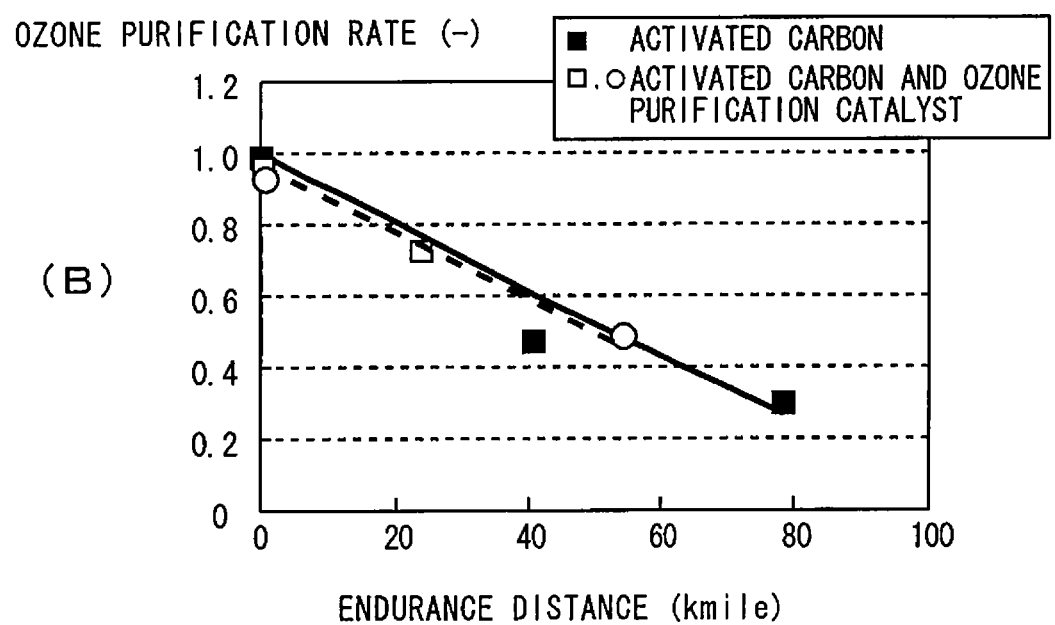

FIG. 8 is a data showing results of an ozone purification endurance test. In FIG. 8, the horizontal axis represents an endurance distance (in kilomiles) and the vertical axis represents a relative value based on an ozone purification rate at an initial state (when the endurance distance is 0 kilomiles). The data shown in FIG. 8 is obtained by preparing activated carbon which supports particles of ozone purification catalyst in dispersed form (see FIG. 7(A)) and activated carbon without supporting ozone purification catalyst (their sizes and specific surface areas are equivalent), and then measuring the rear side ozone level of the two activated carbons by blowing a gas which contains ozone with a predetermined level through these activated carbons from the front side toward the rear side at different velocities (wind velocities of 1 m/s and 10 m/s).

FIG. 8 shows not only data obtained by the activated carbon supporting ozone purification catalyst particles in dispersed form but also data in FIG. 3 for comparing therewith. Incidentally, the data shown in FIG. 3 is indicated as the relative value based on the ozone purification rate at the initial state of the activated carbon on which the ozone purification catalyst particles are supported in dispersed form. FIG. 8(A) is data obtained by blowing the gas at the wind velocity of 1 m/s, and FIG. 8(B) is data obtained by blowing the gas at the wind velocity of 10 m/s. From FIG. 8(A), it is found that the activated carbon with the ozone purification catalyst particles is suppressed in regard to degradation of ozone purification rate as compared to the one without the ozone purification catalyst particles. That is to say the data in FIG. 8(A) supports the fact that ozone was purified by the ozone purification catalyst particles. From FIG. 8(B), however, it is found that the these activated carbons are equal in regard to degree of the degradation of ozone purification rate regardless of the presence or absence of the ozone purification catalyst particles. That is to say the data in FIG. 8(B) indicates that the reactions carried out in the ozone purification catalyst (i.e. the reactions represented by the expressions (5) to (7)) progress inadequately under a condition of high wind velocity.

In view of this, when the ozone purification catalyst layer 26 is formed on the surface of the activated carbon 24, ozone in the atmosphere can definitely contact with the ozone purification catalyst layer 26. In addition, it enables to purify the active oxygen generated by the ozonolysis reaction with the activated carbon promptly by the ozone purification catalyst located near the generated active oxygen. Therefore, the reactions carried out in the ozone purification catalyst can be enhanced thereby the life of the ozone purifying element can be extended even under a condition of high wind velocity.

[Method for Manufacturing the Atmosphere-Cleaning Device Equipped on Vehicle]

Figure 9:
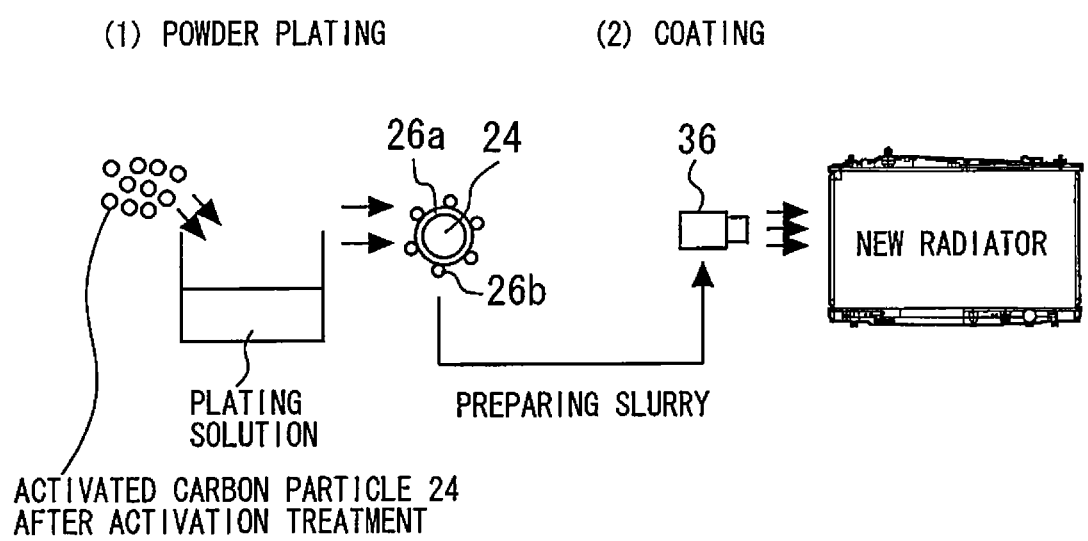
FIG. 9 is a manufacturing flowchart of the radiator 14 of FIG. 1.

Next, a method for manufacturing the atmosphere-cleaning device of the present invention will be explained with reference to FIGS. 9 and 10. FIG. 9 is a manufacturing flowchart of the radiator 14 of FIG. 1. As shown in FIG. 9, the radiator 14 of FIG. 1 is manufactured by undergoing a powder plating process (1) and a coating process (2).

The powder plating process (1) is a process where the ozone purification catalyst layer 26 is formed on the surface of the activated carbon particle 24 by electroless plating process. Specifically, at first, the activated carbon particle 24 is dipped into a first plating solution (for example, Co plating solution) after an activation treatment with Pd colloid particle and the like thereby the surface of the activated carbon particle 24 is covered with a first catalyst element 26a. Secondly, the covered particle is dipped into a second plating solution (for example, Ag plating solution) thereby the surface of the covered particle is covered with a second catalyst element 26b. Then, a particle of an ozone purifier shown in FIG. 9 is obtained.

The coating process (2) is a process where the ozone purification layer 22 is coated on a core part of a new radiator by spraying. Specifically, at first, the particles of ozone purifier obtained by undergoing above mentioned process (1) are dispersed in a binder to prepare slurry. Secondly, the slurry is coated on the core part of the new radiator by using a spray 36. Finally, the binder is dried to be removed and then the radiator 14 is manufactured.

Figure 10:
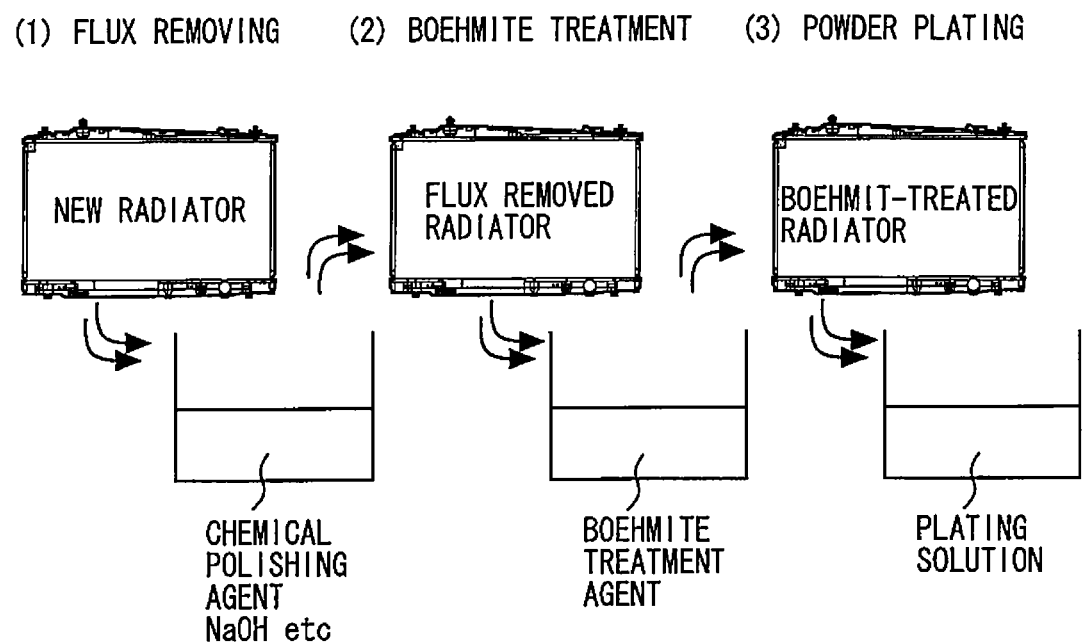
FIG. 10 is a conventional manufacturing flowchart for comparing with the flowchart of FIG. 9.

FIG. 10 is a conventional manufacturing flowchart for comparing with the flowchart of FIG. 9. Considering to recent distribution of radiators, it is unrealistic to form the ozone purifier layer on the radiators at the time of manufacturing. From the cost front, it is desirable to form the ozone purifier layer on the radiators in direct, not to form by taking new radiators apart. Here, the ozone purifier layer can be formed on the radiators in direct by electroless plating. However, flux is generally used to a radiator for the purpose of jointing the components of the radiator such as fins and tubes, which inhibits the formation of the ozone purifier layer in electroless plating. Therefore, a chemical polishing process (a flux removing process (1)) had been needed to remove the flux, which led to a problem of worsening in productivity.

Moreover, to form the ozone purifier layer, the radiators had been subjected to a boehmite treatment (a boehmite treatment process (2)) and then dipped into an electroless plating solution (electroless plating process (3)). In other words, including above-mentioned flux removing process, chemical treatments with chemical agents are performed successively. And thus, there have been problems of increase in number of processes and labor.

According to the flowchart shown in FIG. 9, above-mentioned flux removing process is not needed and the electroless plating process can be finished during the preparation stage of raw material of the ozone purifier. Therefore, it can contribute to lowering the number of process and suppressing the problem of worsening in productivity. Also, the flowchart shown in FIG. 9 makes it possible to manufacture the radiator 14, by spraying, on which the ozone purifier layer 22 is formed with intended layer thickness and uniformly-dispersed particles of the ozone purifier.

Other Embodiments

In above-mentioned embodiment, the ozone purification catalyst layer 26 is arranged so as to cover around the activated carbon particle 24. However, the ozone purification catalyst layer 26 may not always be formed on each of the activated carbon particle 24 nor be formed around the activated carbon particle 24. In other words, the ozone purification catalyst layer 26 may be formed partially on the activated carbon particle 24.

In above-mentioned embodiment, the ozone purifier includes activated carbon. However, the composition of the ozone purifier may be modified in the following three ways.

Firstly, zeolite may be used instead of activated carbon. Since zeolite has a high specific surface area as well as activated carbon, a lot of the first catalyst element 26a and the second catalyst element 26b can be supported thereon. Also, zeolite has a function of purifying ozone, although the level is lower than activated carbon. Therefore, if the ozone purification catalyst layer 26 is formed on the surface of zeolite, the life of the ozone purifying element can be extended, as well as the embodiment, even under a condition of high wind velocity. Zeolite may be used with activated carbon.

Secondly, oxidized iron, titania, alumina or silica may be used instead of activated carbon. Although its specific surface area is low, oxidized iron, titania, alumina or silica has a function of purifying ozone equivalent to activated carbon. Therefore, if oxidized iron etc. are used instead of activated carbon, they promise a certain level of ozone purification. Oxidized iron etc. may be used with activated carbon.

Thirdly, the ozone purifier may include only the ozone purification catalyst instead of including activated carbon. Since ozone purification catalyst has a function of purifying ozone independently, it promises a certain level of ozone purification. When the ozone purifier includes only the ozone purification catalyst, the particle has a structure with the first catalyst element 26a as a core and the second catalyst element 26b supported on the surface of the core.

DESCRIPTION OF REFERENCE NUMERALS 10 vehicle
12 internal combustion
14, 28 radiator
16 capacitor
18 bumper grill
20 base material
22 ozone purifier layer
24 activated carbon particle
26 ozone purification catalyst layer
26a first catalyst element
26b second catalyst element
32 activated carbon layer
34 ozone purification catalyst particles

The invention claimed is:

1. An atmosphere-cleaning device equipped on vehicle, comprising:
    an on-vehicle component arranged on a portion where an air flow passage is formed while a vehicle is moving; and
    an ozone purifier provided on a surface of the on-vehicle component,
    wherein said ozone purifier includes
        a particle of activated carbon, and
        an ozone purification catalyst which covers a surface of the particle of activated carbon and contains two or more metals each of which has a different standard electrode potential, and
    wherein the ozone purification catalyst includes a first catalyst element which is arranged so as to cover around the particle of activated carbon, and a second catalyst element which is supported on a surface of the first catalyst element.

2. The atmosphere-cleaning device equipped on vehicle according to claim 1, wherein
    said on-vehicle component is a radiator, and
    said ozone purifier is a single layer formed on the surface of said radiator.

3. The atmosphere-cleaning device equipped on vehicle according to claim 2, wherein
    the ozone purifier is formed on a core part of the radiator.

4. The atmosphere-cleaning device equipped on vehicle according to claim 1, wherein
    a main element of the first catalyst element is at least one metal selected from the group of Co, Ni, Cu, Fe, Sn, Rh, Ir, Pd, Pt, Ag, Au, Ru and Os, and
    a main element of the second catalyst element is a metal with higher standard electrode potential than the metal used as the main element of said first catalyst element.

5. A method for manufacturing an atmosphere-cleaning device equipped on vehicle according to claim 1, comprising:
    preparing an ozone purifier, by electroless plating process, which includes an ozone purification catalyst containing two or more metals each of which has a different standard electrode potential and a particle of activated carbon whose surface is covered with said ozone purification catalyst; and
    preparing slurry said ozone purifier and applying the slurry, by spraying, on the surface of said on-vehicle component.

6. The method for manufacturing an atmosphere-cleaning device equipped on vehicle according to claim 5, wherein
the electroless plating process is a powder plating process including:
performing an activation treatment of the particle of activated carbon,
dipping the particle of activated carbon into a first plating solution to cover a surface of the particle of activated carbon with a first catalyst element, and
dipping the particle of activated carbon covered by the first catalyst element into a second plating solution including a second catalyst element so that the second catalyst element is supported on a surface of the first catalyst element.

\* \* \* \* \*